United States Patent [19]

Oxley

[11] Patent Number: 5,284,772
[45] Date of Patent: Feb. 8, 1994

[54] SPECIMEN COLLECTION AND ANALYSIS BAG

[75] Inventor: L. Thomas Oxley, Riverwoods, Ill.

[73] Assignee: T Systems Inc., Riverwoods, Ill.

[21] Appl. No.: 662,612

[22] Filed: Feb. 27, 1991

Related U.S. Application Data

[63] Continuation-in-part of Ser. No. 509,257, Apr. 13, 1990, Pat. No. 5,084,041, and a continuation-in-part of Ser. No. 534,446, Jun. 6, 1990, and a continuation-in-part of Ser. No. 550,641, Jul. 10, 1990, Pat. No. 5,160,329, and a continuation-in-part of Ser. No. 583,293, Sep. 17, 1990.

[51] Int. Cl.⁵ .............................................. G01N 35/02
[52] U.S. Cl. ...................................... 436/47; 436/43; 436/48; 436/807; 422/63; 422/65; 422/100; 422/103
[58] Field of Search ............... 422/102, 100, 103, 104, 422/99, 63, 81-83, 83.5, 88-89, 65; 436/174, 180, 43, 47, 48, 49, 807; 141/329, 330

[56] References Cited

U.S. PATENT DOCUMENTS

| | | | |
|---|---|---|---|
| 3,239,104 | 3/1966 | Scholle | 222/81 |
| 4,109,829 | 8/1978 | Kuckens et al. | 222/81 |
| 4,458,733 | 7/1984 | Lyons | 141/1 |
| 4,595,562 | 6/1986 | Liston et al. | 422/65 |
| 4,607,671 | 8/1986 | Aalto et al. | 141/329 |
| 4,776,488 | 10/1988 | Gurzan | 222/81 |
| 4,808,381 | 2/1989 | McGregor et al. | 422/100 |
| 4,812,293 | 3/1989 | McLaurin et al. | 422/69 |
| 4,951,512 | 8/1990 | Mazza et al. | 73/861.23 |
| 5,012,845 | 5/1991 | Averette | 141/329 |
| 5,151,184 | 9/1992 | Ferkany | 210/514 |

*Primary Examiner*—James C. Housel
*Assistant Examiner*—Long V. Le
*Attorney, Agent, or Firm*—Reinhart, Boerner, Van Deuren, Norris & Rieselbach

[57] ABSTRACT

An automated method of using a system for sampling and testing a fluid specimen including an analysis station comprising collecting the fluid specimen in a flexible container having an access port, piercing a housing of the access port, withdrawing the piercing element and allowing the fluid specimen to drain from the container.

9 Claims, 10 Drawing Sheets

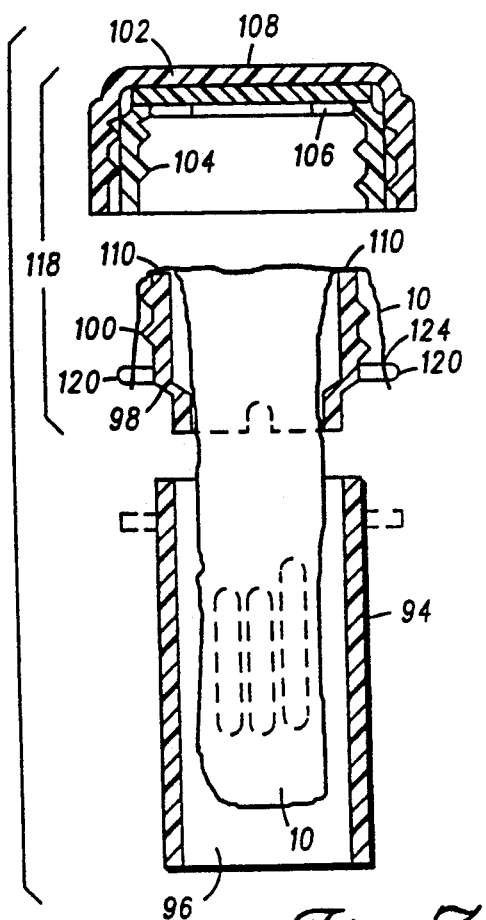
Fig. 7A
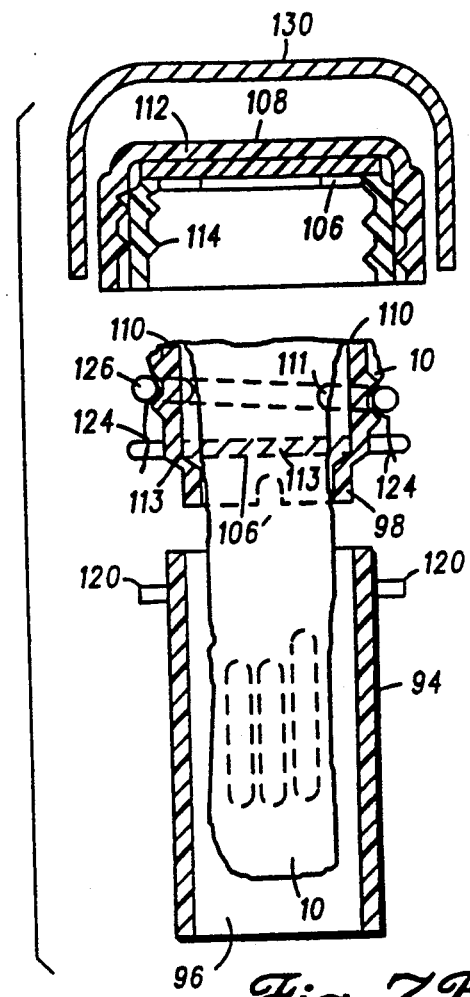
Fig. 7B
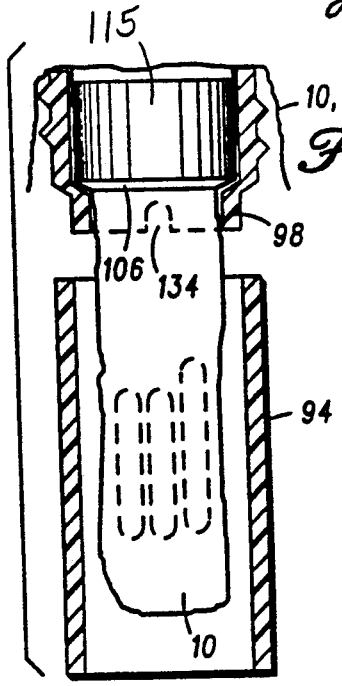
Fig. 7D
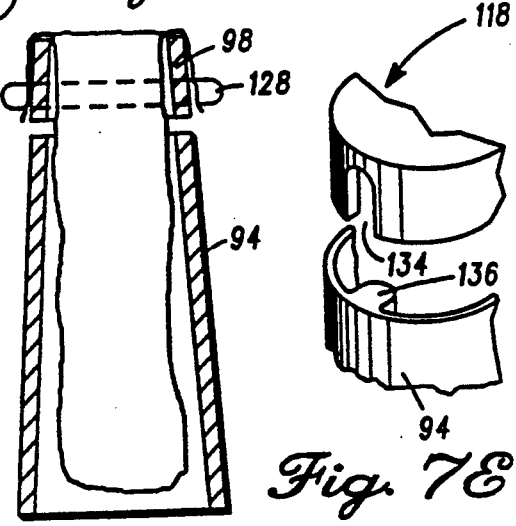
Fig. 7C
Fig. 7E

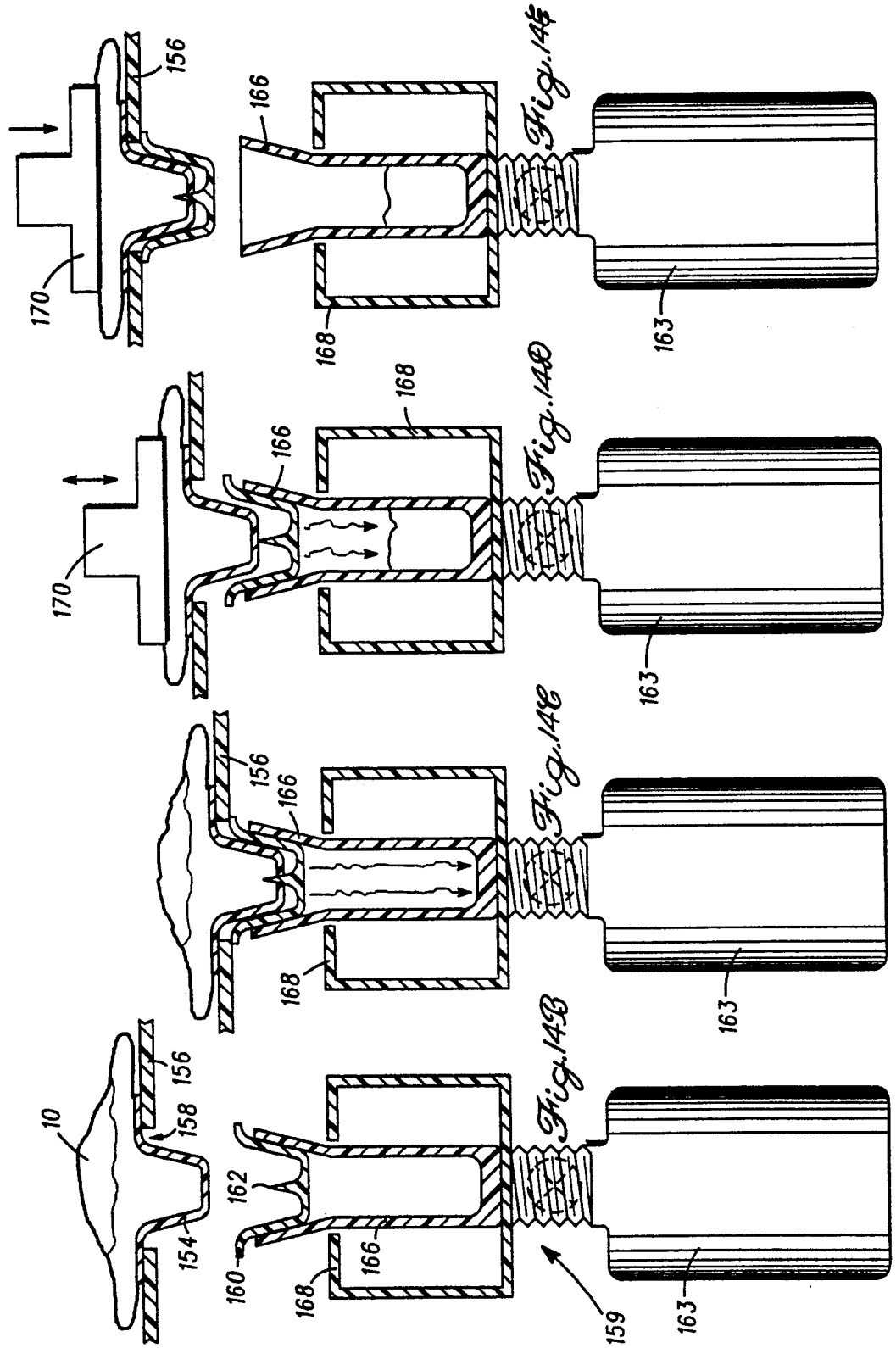

SPECIMEN COLLECTION AND ANALYSIS BAG

This is a continuation-in-part of the following applications: application Ser. No. 07/509,257, filed Apr. 13, 1990, now U.S. Pat. No. 5,084,041, pending application Ser. No. 07/534,446, filed Jun. 06, 1990, application Ser. No. 07/550,641, filed Jul. 10, 1990, now U.S. Pat. No. 5,160,329, and pending application Ser. No. 07/583,293, filed Sep. 17, 1990.

The present invention is concerned generally with a container for accumulating and dispensing a fluid specimen for chemical processing or analysis. More particularly, the invention is concerned with a system using a container for accumulating and/or dispensing fluid specimens for analysis to ascertain the presence of undesirable chemical and/or biological substances.

Analysis for undesirable substances in a specimen involves collection and/or dispensing, and also analysis of a specimen, typically a fluid. Labels can be attached to the exterior of the container and/or to a coupled remote or holding container in selected instances. A lab technician can include on the label the source of the specimen, the date of collection and other relevant data for use in analysis of the specimen. Analysis of any specimen using a container usually requires additional preparatory steps, including, for example, (a) creation of a new record of information for each analytical procedure performed on the specimen, and in some instances also maintaining the legal chain of evidence for the specimen, (b) physical apportionment of the initially collected specimen into a plurality of specimens for a number of different analytical evaluations, and (c) maintenance of the chemical integrity of the specimen during and after subdivision into a plurality of specimens undergoing different tests in the analytical process. There is a strong and growing demand for large scale testing programs, such as for environmental and food product specimens by various corporations and governmental agencies. Such a substantial increase in the demand for testing programs will place a great premium on improved economics, efficiency and reliability, and in some cases will require strict integrity of the legal chain of specimen custody.

It is therefore an object of the invention to provide an improved method and system for accumulating a specimen for ascertaining the presence of undesired substances and/or diseases.

It is another object of the invention to provide a novel specimen system for transferring specimens to and/or from a multicompartment plastic container for chemical and disease control analysis.

It is a further object of the invention to provide an improved system for reliably sealing a plastic container, while prevent unsealing and tampering with the specimen.

It is an additional object of the invention to provide various devices attached to a plastic bag enabling the easy transfer of a specimen to and/or from a plastic container for chemical or disease analysis.

It is yet another object of the invention to provide an improved system using a plastic bag having dispenser elements and access parts which allow destructive access through the container to the specimen.

It is yet a further object of the invention to provide an improved system for transferring fluid specimens from a plastic container using one of a breakaway cap, a twist open seal cap with tamper evident features, an access port couplable to a piercing device and a test tube sealingly coupled to an access port of the container.

It is an additional object of the invention to provide a novel fluid specimen container and processing system for accumulating fluid specimens and selectively accessing the specimen in the container with a piercing device enabling automated dispensing to an analytical receptacle for automated analysis.

It is still an additional object of the invention to provide an improved disposable funnel for collecting a fluid specimen in a plastic bag having a plurality of subcompartments disposed within a substantially rigid confinement structure.

Other objects, features and advantages of the present invention will be readily apparent from the following description of the preferred embodiments thereof, taken in conjunction with the accompanying drawings described below wherein like elements have like numerals throughout the several views.

DESCRIPTION OF THE DRAWINGS

FIG. 7A illustrates a plastic bag support and sealing system in an exploded view, FIG. 7B shows the system of FIG. 7A including a tamper evident seal, plastic bag retention elements and an alternate bag sealing structure; FIG. 7C illustrates a tapered sealing unit and support structure for receiving an elastic ring to retain a plastic bag; FIG. 7D illustrates a further alternative bag sealing structure; FIG. 7E shows a keyway and key element for locking relative movement of the sealing unit and support structure;

FIG. 14A illustrates a puncture and draining element in side cross section and top view and FIGS. 14B-14E show a method of using one of the access ports in FIG. 13A to access a specimen by means of the puncture element of FIG. 14A.

DETAILED DESCRIPTION OF PREFERRED EMBODIMENTS

Figure 1:
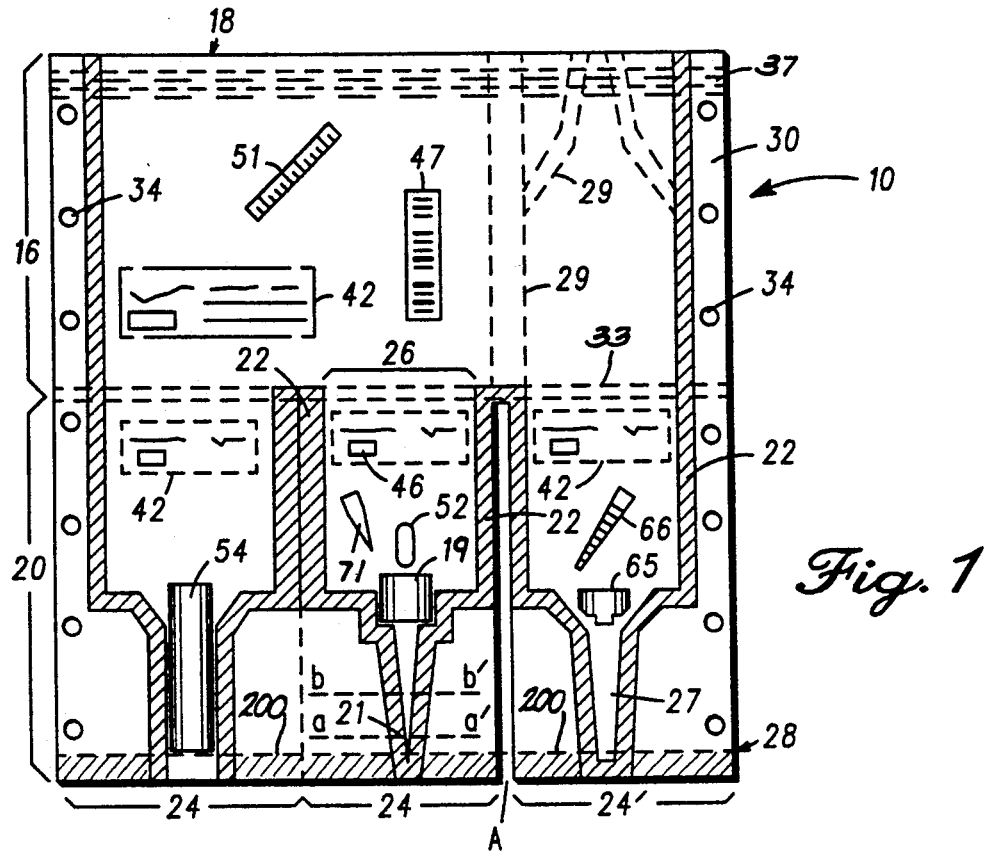
FIG. 1 is a front elevation of a multicompartment plastic bag constructed in accordance with one form of the invention.
Figure 13A:
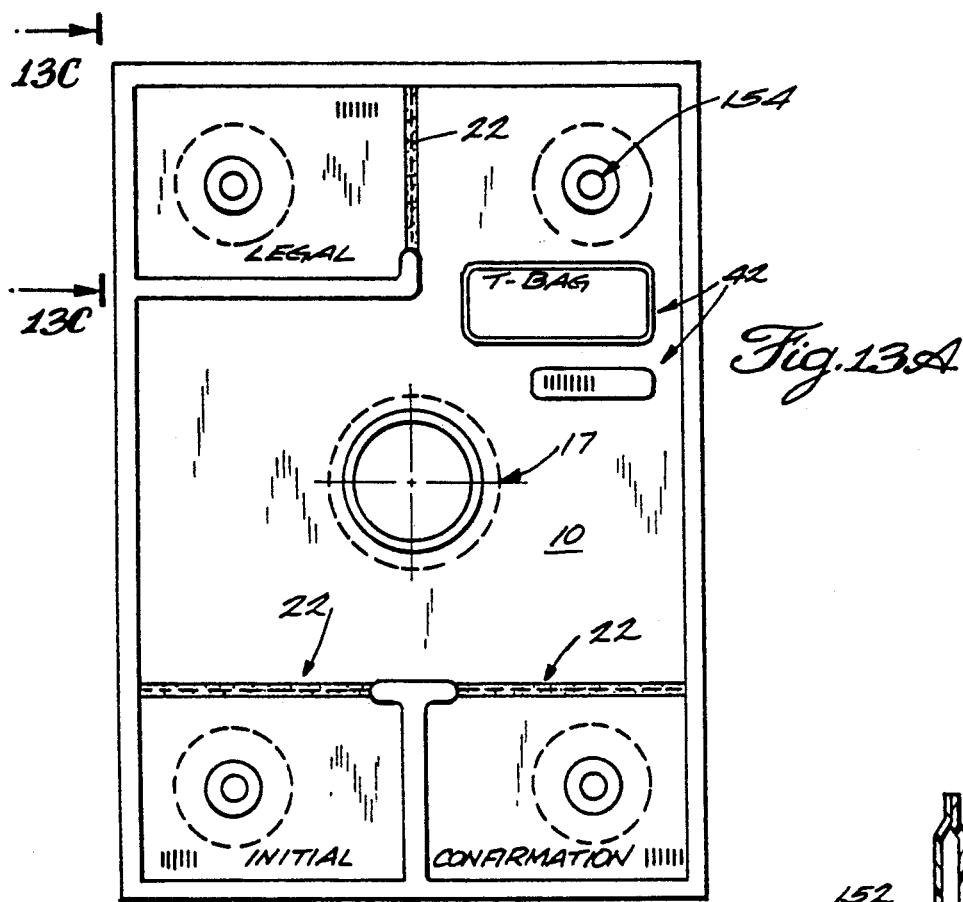
FIG. 13A shows a plastic bag in a plan view with various access ports.
Figure 13C:
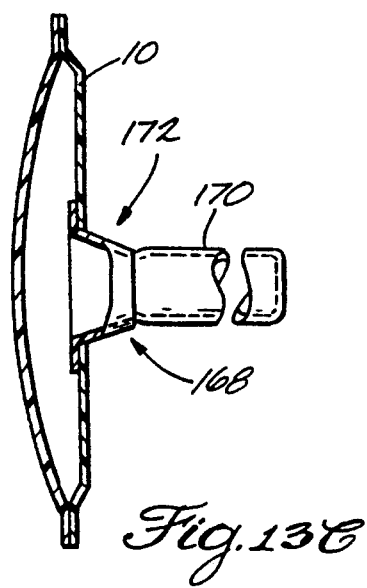
FIG. 13C shows a partial side view of another one of the access ports shown along section cross section taken along 13C—13C in FIG. 13A.

Referring to the drawings and in particular to FIGS. 1, 2 and 13, a multicompartment plastic container, such as a plastic bag 10, constructed in accordance with the invention is generally indicated. Collection and analysis of specimens having undesirable (or conversely, specifically desired) chemicals or biological substances (hereinafter all of the above are an "undesirable substance") is accomplished by utilizing the illustrated multicompartment plastic bag 10 (hereinafter "the plastic bag 10"). In order to carry out determination of the presence of an undesirable substance, the plastic bag 10 functions first to collect a specimen taken from the subject source, such as cow's milk or water from a polluted body of water. Various means can be used to effectuate collection of the specimen. For example, collection of a specimen can be accomplished as shown in FIG. 3A by using a funnel 11. Alternatively, as shown in FIG. 3B one can use a funnel 14 comprised of a cardboard stiffener 12 and plastic liner 13. In either case the plastic bag 10 can be disposed within a support container 15A or 15B.

The plastic bag 10 includes an upper bag section 16 having an opening at one end (shown generally as 18 in FIG. 1) to enable receiving the fluid specimen potentially containing the undesirable substance. Accumulation of the specimen is accomplished by inserting the plastic bag 10 into the support container 15A with the open end 18 positioned at the top of the support container 15A. Alternatively in FIG. 3B an open flange 17 is sealingly engaged to the plastic bag 10 and supports the top of plastic bag 10 outside the container 15B. Once the specimen has been collected, a seal cap 108 (see FIG. 13B) can be sealingly coupled to the flange 17.

In the embodiment of FIG. 3A, the funnel 11 is then pushed into the support container 15, and the plastic bag 10 is in position to receive and accumulate the fluid specimen. Once the fluid specimen has been collected in the plastic bag 10, the funnel 11 can be removed and discarded. While the plastic bag 10 is still within the support container 15A, or alternatively after removal of the plastic bag 10 from the support container 15A, the accumulated fluid specimen can be moved within the upper bag section 16 to apportion the undesired substance. This apportionment can take place in both the upper bag section 16 and selected portions of the lower bag section 20. In the preferred embodiment the plastic bag 10 can be sealed at the top to preserve the specimen integrity before apportioning the specimen in the various bag sections or subcompartments. In an alternative embodiment one can choose to apportion the fluid specimen between the bag sections before sealing at the top.

The ability to apportion the collected fluid specimen among the various bag sections enables establishing a plurality of different specimens for scientific reliability and legal requirements. The apportionment also can be useful if some prescreening tests are to be done on the fluid specimen to eliminate the need to perform complete testing on a large number of specimens.

Figure 2A:
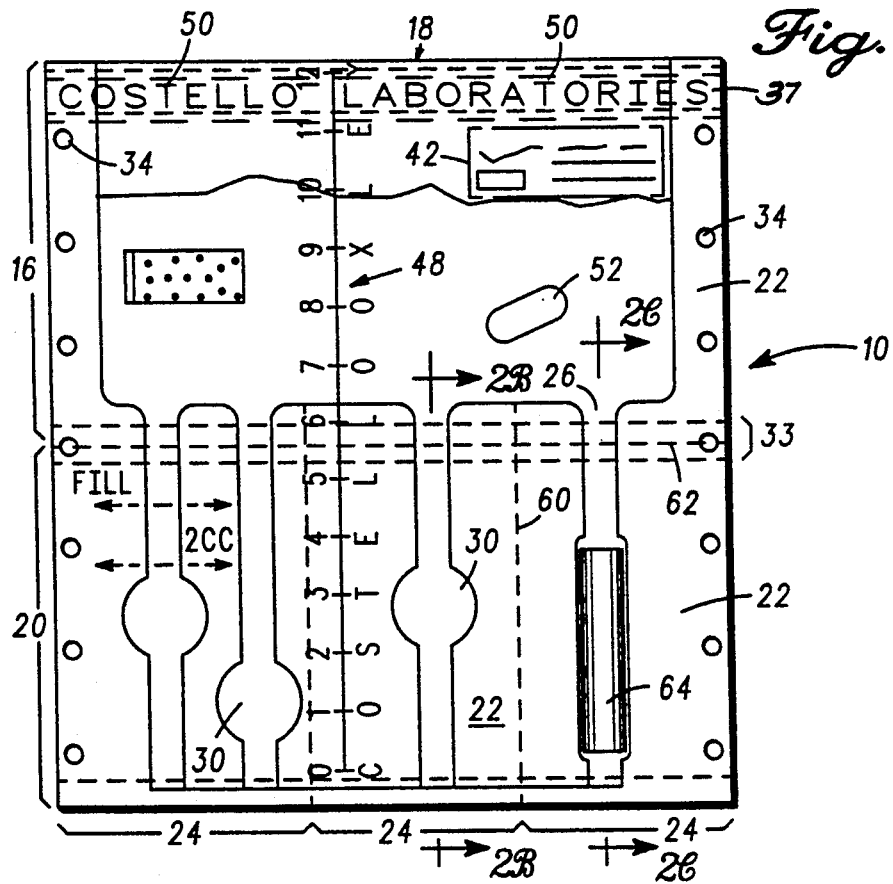
FIG. 2A illustrates a front elevation of a multicompartment plastic bag having a plurality of pouch or pocket elements.
Figure 3A:
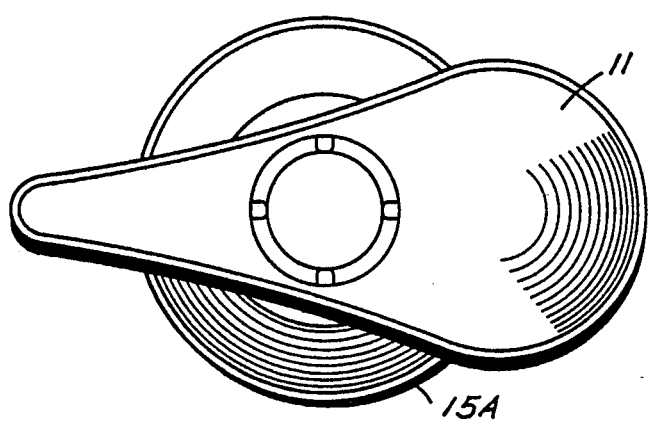
FIGS. 3A and 3B show a funnel and container holding the multicompartment plastic bag for receiving, collecting and transferring a specimen.
Figure 3B:
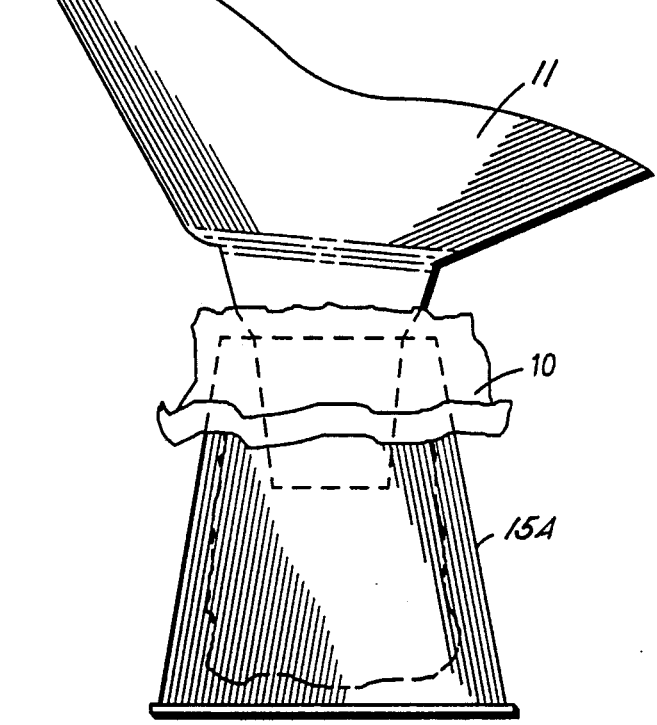

To accomplish the apportionment of the fluid specimen within the various bag sections, the lower bag section 20 is initially at least partially open to the upper bag section 16 via, for example, opening 26 as shown in FIG. 2A. These openings are defined by noting the location of cross-hatched seal areas 22 in the lower bag section 20 as shown in FIG. 1. In the preferred embodiment these seal areas 22 are nonreusable heat seals formed by the manufacturer prior to shipment to the customer and accomplished by use of any one of a variety of conventional available devices, such as heat sealing the plastic. Access to the fluid specimen must therefore proceed by a destruction of some part of the plastic bag 10.

As seen in FIG. 2, the bag design can accommodate various subcompartments 24 in the lower bag section 20 and provide the opening 26 between the upper and lower bag sections, 16 and 20, respectively. One can also use the seal areas 22 to provide different design configurations of subcompartments and even provide additional shapes adjunct to the subcompartments, such as a spout 27 for the subcompartments 24 (see FIG. 1). the spout 27 is usable by merely cutting along one line chosen anywhere above a lower seal line 28 and across the mouth of the spout 27.

In another form of construction of the plastic bag 10, the spout 27 can be accessed by merely tearing along a line of perforations 200, such as along line 28 as shown in FIG. 1. In this manner, one can manually remove part of the plastic bag 10, and thus one does not have to use scissors or any cutting implement which might be contaminated from previously opening a bag containing a fluid specimen having a contaminant therein.

In addition to the illustrated layout for the bag seal areas 22 provided by the manufacturer, the customer, or even the analytical laboratory user, can select alternative seal designs which can be implemented by various known means. A customer can thus select and prepare a custom design by using a predetermined bag size and a conventional manually operating heat sealing device 36 (see FIG. 4C) having a seal bar design in the intended geometry of the final seal areas 22. The plastic bag 10 can therefore include a plurality of different optional heat seal line patterns 29 (see FIG. 1) disposed on at least one of the plastic sheets comprising the plastic bag 10. One can, for example, use different seal line markings (dashed, dotted, and color encoded) to denote different available seal patterns. The various heat seal line patterns 29 can then be implemented by, for example, (a) using manually guided heat seal means, (b) using the heat sealing device 36 having an appropriate seal design pattern (described above), (c) employing a conventional machine control system to perform heat seal line tracing which seals along one of the given marked seal line patterns 29 or (d) using other sealing means creating nonreusable seals.

The ability to construct a variety of functional shapes as part of, and in combination with, the plastic bag 10 can further include, for example, a pipette design 21 in FIG. 1; and also see the features of FIGS. 13 and 14. In FIG. 1 once the opening 26 of the plastic bag 10 has been sealed to form a subcompartment 24 filled with the fluid specimen, the pipette design 21 in FIG. 1 allows dispensing small portions of the fluid specimen. This can be done by first cutting along the lower seal line 28 (or along lines aa' or bb' for larger openings). In an alternate embodiment discussed hereinbefore, the user can manually separate the plastic bag 10 above the lower seal line 28 by virtue of the perforations 200.

Figure 2B:
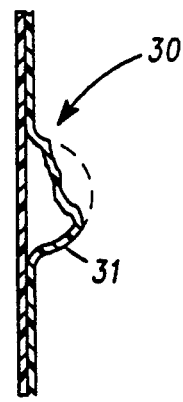
FIG. 2B is a side elevation taken along line 2B—2B of the plastic bag shown in FIG. 2A.
Figure 2C:
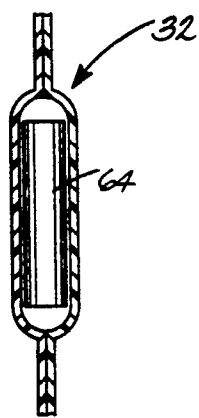
FIG. 2C is a side elevation taken along lines 2C—2C in FIG. 2A.

Tubing 19 (center bottom of FIG. 1) provides support for the surrounding plastic bag 10 and enables controllably displacing substances in the center subcompartment 24 and dispensing small portions of the specimen for testing. Such a pipette type of combined shape can be used with other conceivable designs to enhance bag operation and analysis of the specimen. Further useful shapes can also include, for example, a pocket or pouch element 30 in the lower bag section 20 (see FIGS. 2A–C). This pouch element 30 is defined by at least one plastic layer portion 31 being discontinuous relative to the plane of the plastic sheets of the plastic bag 10. That is, as best seen in FIG. 2B, the pouch element 30 includes the layer portion 31 which deviates from the relatively smooth surface defined by the twin sheets forming the plastic bag 10. The pouch element 30 is fillable with the specimen to provide a locally enlarged substance volume and increased substance optical path length. This structural feature therefore allows accumulation of sufficient substance quantities to perform analytical procedures not normally accomplishable with the relatively thin layers and unknown layer thicknesses of the specimen present within the plastic bag 10.

Additional functional shapes therefore allow well controlled analysis of known specific volumes and known particular optical path lengths of the specimen. The analytical technician can also easily remove, by means such as a syringe or pipette, a substantial and known volume of the specimen. To this end the plastic bag 10 also lends itself to inclusion of various precise volume indicators imprinted in association with the pouch element 30 (see, for example, FIG. 2A left most subcompartment 24 with the 2 cc indicator marking).

Other shapes can also be fabricated, such as a cylindrical pouch 32 (see FIG. 2C), in order to provide a fit within mating receptacles of various types of conventional analytical equipment, such as apparatus originally designed to analyze the specimen retained within conventional test tubes or other conventional sample containers. The cylindrical pouch 32 can further include rigid or semi rigid shapes, such as the cylindrical tube 64. Further details of this advantageous shape feature will be described with more particularly hereinafter.

The subcompartments 24 defined by the design of the plastic bag 10 can be selectively filled in the manner described hereinbefore: the technician can move the specimen between the upper bag section 16 and lower bag section 20 and then through the openings 26 into each of the desired subcompartments 24. Either before or after the technician has apportioned the specimen in the desired sections of the plastic bag 10, the conventional plastic sealing device 36 (see FIG. 4C) or other means for making a seal which cannot be reused, can be used to seal the lower bag section 20. This is accomplished by sealing along center seal area 33 as shown in FIG. 2A. In addition, as described hereinbefore, the plastic bag 10 can be completely closed by sealing the upper seal area 37.

The technician can commence the substance analysis process by separating selected ones of the subcompartments 24 and/or the upper bag section 16. Separation occurs by destructive means and can be accomplished by, for example, cutting with scissors or separating along a prepared tear line. In an alternate embodiment as discussed hereinbefore, the user can manually separate the plastic bag 10 along the lower seal line 28 by virtue of the perforations 200. In another form of the invention the subcompartments 24 can be removed by merely cutting along one line since they are already separated by the manufacturer along another line (see, for example, open area denoted A for subcompartment 24' in FIG. 1).

Figure 4A:
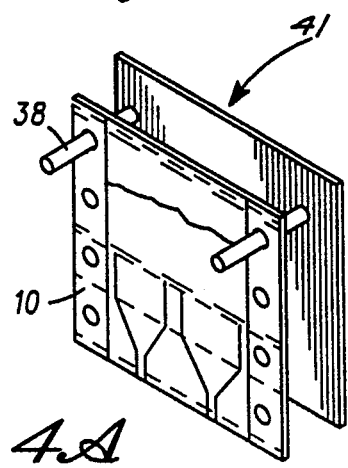
FIG. 4A illustrates a support or storage rack for holding a multicompartment plastic bag.
Figure 4B:
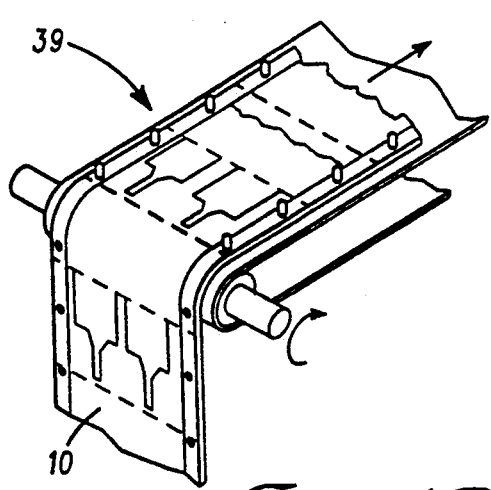
FIG. 4B shows a conveyor system for transporting the plastic bag for analysis of the specimen contained therein and FIG. 4C shows a heat sealing device for closure of the plastic bag and forming selected heat seal areas on the plastic bag.
Figure 4C:
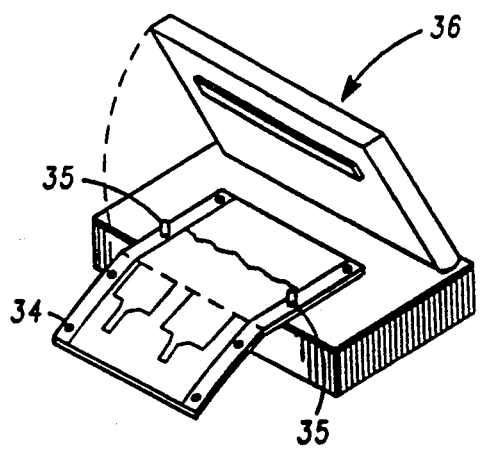

In a preferred form of the invention, the plastic bag 10 also includes holes 34 punched in the perimeter seal region 30 of the plastic bag 10 (see FIG. 1). The holes 34 can be used to assist in expediting evaluation of the specimen in the plastic bag 10. For example, the plastic bag 10 can be hung on locating pins 35 of the heat sealing device 36 (see FIG. 4C). In addition, as shown in FIG. 4A the holes 34 allow hanging the plastic bag 10 on a storage rack 41 having one or more hanging rods 38 to await specimen analysis or for long term refrigerated or frozen storage. Such a storage rack 41 conserves storage space allowing large numbers of specimens to be maintained in a very small volume. The holes 34 also enable coupling of the plastic bag 10 to a conveyor system 39 for transport and subsequent analysis of the specimen (see FIG. 4B).

The plastic bag 10 is preferably an optically transparent or visually translucent material allowing use of any one of a variety of conventional optical analysis procedures on the specimen. Such optical analysis procedures can include, for example, simple naked eye observations and optical absorption spectrophotometry. In another form of the invention shown in FIGS. 7A and 7B, an optically transparent top cover 108 also allows selected optical analysis to be performed. Details of this embodiment will be described hereinafter.

The plastic bag 10 and the fittings in contact with the specimen also should be inert to the substance contained therein to avoid chemical modification or contamination. The plastic bag 10 should further allow long-term cold storage and freezing, while maintaining the physical and chemical integrity of the specimen. Numerous conventional thermoplastic materials fulfill these requirements and an example of such a material is "Saran" coated polyester with an exterior coating of polyethylene.

As mentioned generally before, the ability to collect the specimen in the upper bag section 16 and in various ones of the subcompartments 24 enables performance of a plurality of different tests and maintenance of a reference standard or reference substance and backup standards. The upper bag section 16, for example, can be used for holding a substance for preliminary screening or overflow. The specimens in the subcompartments 24 can, for example, be used for preliminary, primary and confirmatory analyses and also for long-term backup analysis. The ability to use numerous subdivided specimens allows a thorough analysis of the specimen. The ability to have a backup specimen provides a sound evidentiary position when needed to legally and scientifically establish the presence of chemicals, diseases, or other undesirable chemicals in a specimen.

Scientific objectives for substance analysis are met by virtue of the redundancy of available specimens, the performance of multiple specimen analyses and maintenance of a reference or backup specimen. Legal objectives are met by providing clear evidence of the identity of a specimen and unbroken chain of custody over the cycle of collection of the specimen and the performance of numerous analytical procedures. This custodial objective is accomplished in part by inclusion of an identification element on any one or more parts of a surface of the plastic bag 10. The identification element can be, for example, a writeable area 42 for entering information identifying the source of the specimen, a signature box for the donor and locations for entry of the identity and signature of each party in the chain of specimen custody. This writeable area 42 also is preferably on each of the separate sections of the plastic bag 10 in order to establish identity and custody of each specimen portion. Additional identification can be provided by other means, such as, by bar code serial numbers 46 or labels 47 attached to, or imprinted on, each of the separable bag subcompartments 24 and/or on the upper bag section 16 (see FIG. 1).

In order to prevent tampering with the specimen once it has been collected, the plastic bag 10 includes a first tampering indicator means which can be an embossed or imprinted code 50 along the top seal area 37 of the plastic bag 10 (see FIG. 2A. Such a tampering indicator can be applied after collecting the specimen in conjunction with heat seal closure of the bag 10 by use of the heat sealing device 36 shown in FIG. 4C. In another aspect of the invention the tampering indicator means can extend from the upper bag section 16 to the lower bag section 20. Another such tampering indicator 50 can be, for example, an indelible marking 48 on the plastic bag 10. The tampering indicators 48 and 50 of FIG. 2A exhibit a low symmetry design, such as, a name and a precision line having numerical or letter indicators disposed along the line. Alternatively, a more complex shape or design can be embodied in the bag sheets, such as a personalized "seal" having an appearance which would be notable altered if the plastic bag 10 were tampered with before technician analysis. As in the case of the identifying writeable areas 42, such tampering indicators can be included with each of the separate subcompartments 24 or on the upper bag section 16 in order to minimize the opportunity for any tampering occurring at any stage of the specimen.

Figure 13B:
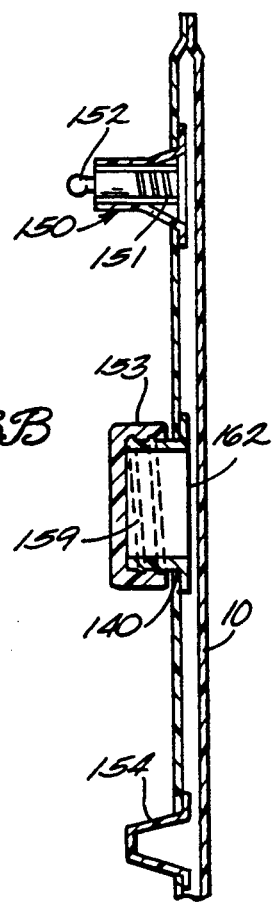
FIG. 13B illustrates a side view of the plastic bag showing the details of the access ports.

Another form of tamper indicator for the plastic bag 10 includes means for access to the fluid specimen by a twist cap 150 shown in FIG. 13B. The twist cap 150 includes an obstruction 152 which must be removed before the twist cap 150 can be turned to allow unsealing of a passage to the fluid specimen, allowing removal of the fluid specimen from the plastic bag 10.

In another aspect of the invention, certain prescreening tests can be performed on the specimen substance in order to diminish the number of "suspect" specimen which must undergo more detailed and costly analysis. Such a prescreening test can be performed on the specimen collected in any of the subcompartments 24 or the upper section 16 of the plastic bag 10. As described hereinbefore in the preferred embodiment, the specimens are apportioned in the subcompartments 24 after the upper bag section 16 is sealed from the outside environment. Once the specimen is apportioned, the subcompartments 24 are sealed and isolated from each other and also from the upper bag section 16. Isolation of the various specimens also can enable testing to proceed on each specimen wholly within the bag which also diminishes the possibility of contamination of the specimen or of disease transmission to a technician performing the analysis.

Prescreening procedures can involve simple tests, such as, checking the temperature of the specimen by use of a conventional thermal strip indicator 51 (see FIG. 1) or checking pH of the specimen by the use of pH sensitive indicator strips. Rather than including the pH strips, the temperature sensors or other such indicators as separate components loosely disposed within the plastic bag 10, such sensors can also be integrally incorporated into the structure of the plastic bag 10, or even included integrally as part of various means for sealing the plastic bag 10. For example, such sensors can be incorporated with transparent windows, such as the top cover 108 shown in FIG. 7 or as part of insert plug 115 (see FIG. 7D).

More complicated prescreening tests can involve the release of one or more analytical reagents in the upper bag section 16 or the subcompartments 24, such as, by opening or breaking a capsule 52 containing an analytical agent (see FIG. 2A). This analytical reagent reacts with the specimen and analytical equipment (not shown) can then be used to carry out the prescreening tests. For example, Enzyme Immunoassay (EIA) can be performed by prefilling two of the capsules 52, one with reagent A and the other with reagent B, and sealing such capsules. At the time of specimen collection, the two capsules 52 (including the reagents A and B for determining the presence of a specific chemical) are inserted into selected parts of the upper bag section 16 or the lower bag section 20. After the specimen has been collected, and the bag sections 16 and 20 sealed from one another, analysis can proceed in the selected bag section by fracturing the capsules 52. The reagents A and B contained in each of the capsules 52 are then released to react with the specimen. The reaction can generate a color change which is related to the chemical concentration in the specimen. This color change can be detected through the optically transparent bag section 16 or 20, either by the naked eye or analyzed in detail by a conventional optical instrument, such as a spectrophotometer (not shown). Separate selected pairs of reagents in the capsules 52 are typically used for detecting each individual chemical. Multiple ones of the subcompartment 24 can be provided in the bag sections 16 or 20, each intended for holding pairs of the capsules 52 for a different chemical analysis. Alternately, a single fracturable multi-compartmented one of the capsules 52 having numerous reagent pairs can be provided in the bag sections 16 or 20. Other conventional prescreening chemical tests are also possible, such as, for example, radio immunoassay analysis, fluorescence polarization immunoassay testing or a modified thin layer chromatography option.

In another form of the invention, the plastic bag 10 further includes a substantially rigid element which can be disposed in at least one particular portion of the bag. For example, the rigid element can be a piece of cylindrical tubing 54, a sample cup 65, or a conical pipette 66, as shown in FIG. 1. One can also choose to have a snug fit for the lower portion of the cylindrical tubing 54, the sample cup 65, or the conical pipette 66 in order to establish a seal to the bag 10. This seal surface will allow specimen handling such that no leakage of the undesired specimen occurs other than by a path through the tubing 54, the sample cup 65 or the pipette 66.

Figure 5:
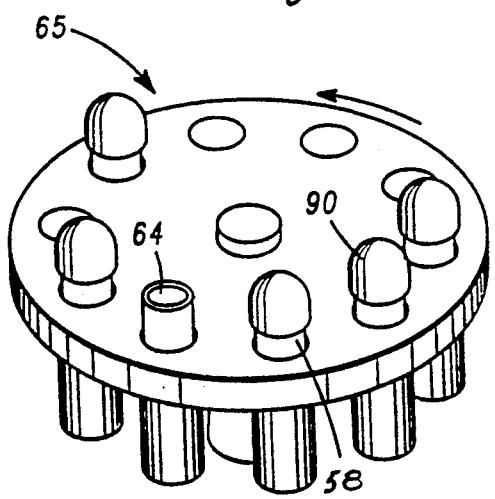
FIG. 5 illustrates a carousel style analytical apparatus having cylindrical receptacles for receiving plastic bag subcompartments including thimble elements disposed on either bag end.

Such a rigid or semi-rigid element structure advantageously also provides a predetermined shape for allowing shape sensitive mechanical handling of the specimen. By establishing this predetermined shape, the specimen can be handled by analytical processes which require fitting the bag portion which holds the specimen into a mating receptacle of the analytical instrument. For example, in the case of the rigid or semi-rigid element being the cylindrical tubing 64 (see FIG. 2A), the specimen is collected in the right most bag subcompartment 24 which is separated from the plastic bag 10 by cutting along seal lines 60 and 62. A resulting separated bag subcompartment 58 containing the specimen and the cylindrical tubing 64 can then be directly inserted into conventional test tube receptacles of a carousel style specimen processing station 65 (see FIG. 5). Using such an analytical processing station, an automated specimen sampling probe or syringe is lowered to retrieve a sample of the specimen for chemical analysis. Therefore, the substantially rigid cylindrical tubing 64 allows the unmodified use of conventional specimen processing equipment for analysis of specimen collected in the plastic bag 10 of the invention. The size and shape of the rigid element can be adjusted for the amount of fluid or biological specimen collected.

Figure 6A:
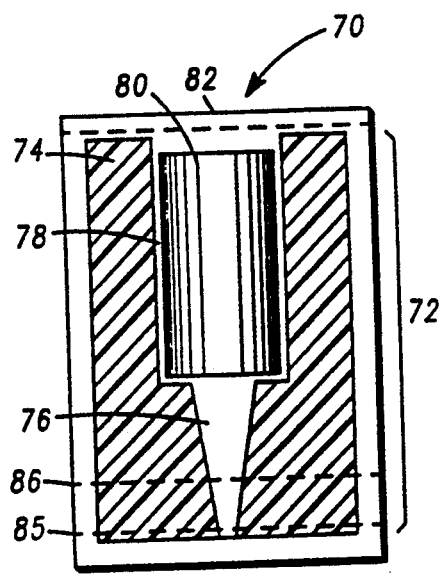
FIG. 6A shows an individual plastic bag containing a semi-rigid element.
Figure 6B:
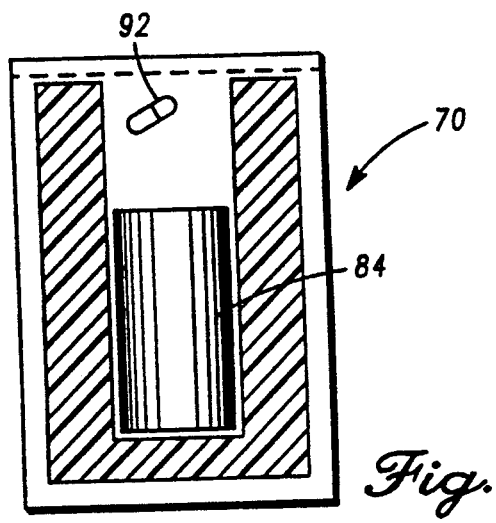
FIG. 6B illustrates an individual plastic bag containing a length of plastic tubing and FIG. 6C shows the bag of 6B with an identification label used to wrap the bag into conformity with the plastic tubing.
Figure 6C:
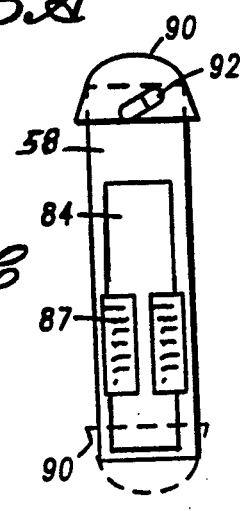

In another form of this invention, the bag subcompartment 58 can further include a thimble element 90 as shown in FIG. 6C. The thimble element 90 is shown disposed on the top end of the cylindrically wrapped bag subcompartment 58, thus providing additional rigidity and control of the cylinder shape, as well as preventing bag unwrapping and formation of unwanted air pockets in the bag subcompartment 58. The thimble element 90 can also be disposed on the bottom of the bag subcompartment 58 as shown in phantom in FIG. 6C. When disposed on the bottom, the thimble element 90 can also maintain the cylindrical test tube shape for use in the carousel processing station 65 (see FIG. 5).

In another aspect of the invention the multicompartment plastic bag 10 can enclose various useful tools, such as, a probe 71 in FIG. 1 for puncturing the spout of the pipette 21 to provide highly controllably release of the specimen or for breaking the capsule 52 used for in situ chemical analysis.

In another form of the invention shown in FIG. 6, an individual plastic bag 70 incorporates advantageous structural elements enabling use for example, as a pipette, test tube and cuvette in specimen analysis. This individual plastic bag 70 can be supplied individually or can be provided as a separable part of the multicompartment plastic bag 10 described hereinbefore. The structural elements included in the individual plastic bag 70 comprise, e.g., a pipette 72 in FIG. 6A. The pipette 72 is constructed by forming heat seal areas 74 in the individual plastic bag 70 to define a conical pipette section 76 and an upper pipette section 78. Within the upper pipette section 78 is disposed a semi-rigid or displaceable component, such as conventional plastic tubing 80. In the embodiment of FIG. 6A the specimen is introduced through an open top 82 which is then sealed to enclose the specimen. This specimen can later be analyzed, and the technician can use the pipette 72 by cutting along one of lines 85 or 86, depending on the flow rate desired. The technician can thus dispense the specimen by squeezing the displaceable tube 80 causing controlled substance removal for analysis.

The individual plastic bag 70 can also be presealed along the top 82, and the bottom is open to the conical pipette section 76. In such a configuration the specimen can be drawn into the individual plastic bag 70 by squeezing the displaceable tube 80, causing a suction action drawing in the specimen or other selected liquids, such as chemical reagents. The individual plastic bag 70 can then be sealed and subsequent specimen analysis performed.

In another feature of the individual plastic bag 70 a semi-rigid element, such as plastic tubing 84, can be placed within the plastic bag 70 as shown in FIG. 6B. The specimen can be introduced into the individual plastic bag 70 which is then sealed. An identification label 87 can also be wrapped around the individual plastic bag 70 which is thus conformed to the shape of the semi-rigid element. In the form illustrated in FIG. 6C the individual plastic bag 70 takes on a cylindrical shape enabling use as a test tube type structure which can be placed into conventional test tube receptacles of automatic analysis equipment (see FIG 5). For such analysis procedures the top of the individual plastic bag 70 is cut open to allow access by a syringe to remove a specimen for analysis or to add test chemicals to determine the presence of selected drugs or biological substances. In addition, optical testing can be performed on the specimen to ascertain the presence of selected chemicals. In the same manner as shown in FIG. 2A the individual plastic bag 70 can include a capsule 92 containing an analytical reagent for chemical evaluation and prescreening evaluation.

Figure 14A:
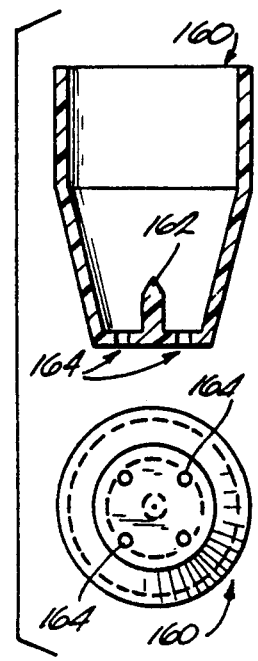

In another variation of this embodiment shown in FIG. 14B, the fluid specimen in the plastic bag 10 can be analyzed by an automated system wherein the specimen is accessed through a port 154 sealingly coupled to the plastic bag 10. The plastic bag 10 is being transported along conveyor 156 having openings 158 which accept the ports 154. At selected locations along the conveyor 156, a sampling station 159 accesses the fluid specimen in the plastic bag 10 by engaging a piercing element 160 to the port 154 shown in detail in FIG. 14B. As shown in FIG. 14A, the piercing element 160 includes a sharp protrusion 162, and the piercing element 160 is moved by engagement device 163 causing the protrusion 162 to pass through the top seal of the port 154. Penetration of the port 154 causes the fluid specimen to pass through orifices 164 into test receptacle 166 (such as a test tube or cup) disposed in an analyzer housing 168. The transfer of a fluid specimen from the plastic bag 10 can also be assisted by a mechanical press 170 which applies pressure to force the fluid specimen into the test receptacle 166. Once sufficient fluid specimen has been accumulated in the test receptacle 166, the engagement device 163 sealingly reengages the piercing element 160 to the port 154. The engagement device 170 is then retracted leaving piercing element 160 sealingly engaged with the port 154. The fluid specimen in the test receptacle 166 is subsequently transported into an analyzer (not shown) for performing appropriate tests. The sampled and resealed plastic bag 10 is transported by the conveyor 156 to a next selected location, such as a storage area or to another test station where a different test can be performed on the already accessed specimen or another one of the redundant fluid specimens in another subcompartment of the plastic bag 10.

In another form of the invention the plastic bag 10 (see FIG. 1) or the individual plastic bag 70 (see FIG. 6) can be held by supporting means, such as cylindrical support member 94 shown in FIG. 7A, during collection of the specimen. The plastic bag 10, 70 is inserted into the cylindrical support member 94 which can be either open or closed at distal end 96. The plastic bag 10 is then pulled through a portion of a mechanical sealing means, such as, cylindrical seal member 98, having a threaded seal portion 100 on the exterior thereof. The plastic bag 10, 70 is folded over the edge of the cylindrical seal member 98 and means for mechanically sealing is used to seal the specimen inside the plastic bag 10. The mechanical sealing means can be, for example, a screw-on cap 102 which includes a threaded cap portion 104 mated to screw on the threaded seal portion 100, a top cover 108 and a seal gasket 106. The seal gasket 106 can be compressed by the screw-on cap 102 to form a seal to the top cover 108 and to seal area 110 on the cylindrical seal member 98. As described hereinbefore, the top cover 108 of the screw-on cap 102 can be selected to be optically transparent enabling inspection and analysis of the specimen in situ and also allow reading of a temperature sensor or pH indicator as described hereinbefore.

Other forms of the mechanical sealing means can also include a snap-on cap 112. As best seen in FIG. 7B, the snap-on cap 112 includes cap protrusion 114 which engages sealing protrusions 109 disposed on the exterior of the cylindrical seal member 98. Once the snap-on cap 112 is engaged, the seal gasket 106 is compressed and provides a seal both to the top cover 108 and to the seal area 110 in substantially the same manner as the embodiment shown in FIG. 7A.

Another variation of mechanical sealing means is shown in FIG. 7D wherein insert plug 115 is seated to compress the gasket 106 to seal the plastic bag 10, 70. In another form of the invention, the insert plug 115 can be composed of a conventional material which also performs the sealing function of the gasket 106, making a separate gasket unnecessary.

Figure 9:
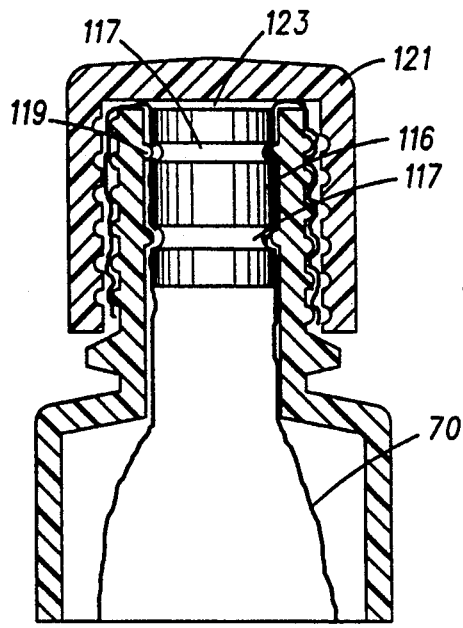
FIG. 9 illustrates a cross sectional view of a seal plug for sealing a plastic bag and insertable in the sealing position by using a screw-on cap.

An additional variation of mechanical sealing means is further shown in FIG. 9 wherein plug 116 effectuates a seal of the individual plastic bag 70. The plug 116 is composed of a material capable of performing a gasket or sealing function, and the plug 116 includes circumferential recesses 117 which sealingly engage inside protrusions 119 on cap 121 with the plastic bag 70 sealed between the plug 116 and the protrusions 119. The cap 121 is used to conveniently drive the plug 116 into the sealing position. In a preferred form the plug 116 further includes an attached soft disk or label 123 having a tacky adhesive material on the portion facing the cap 121. The adhesive coated label 123 thus provides a convenient coupling of the plug 116 and the cap 121, while permitting independent rotation of the cap 121 to seat the plug 116 in a sealing position.

Figure 3C:
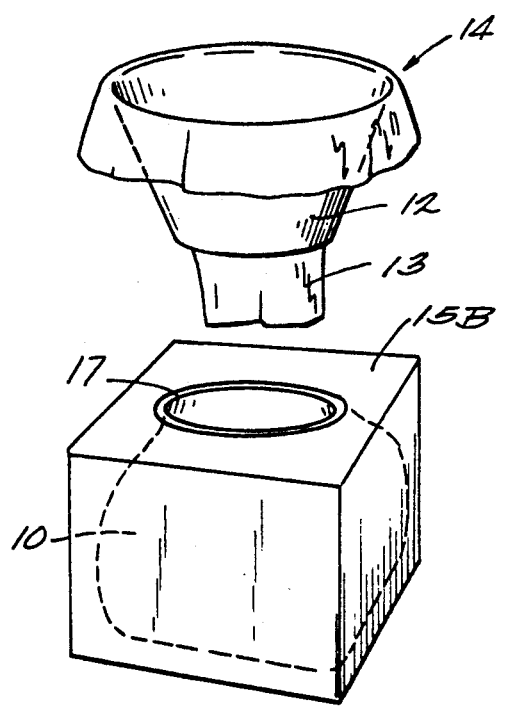
FIG. 3C illustrates a support piece for a plastic lined funnel and a rigid support structure for a plastic bag within the support structure.
Figure 12A:
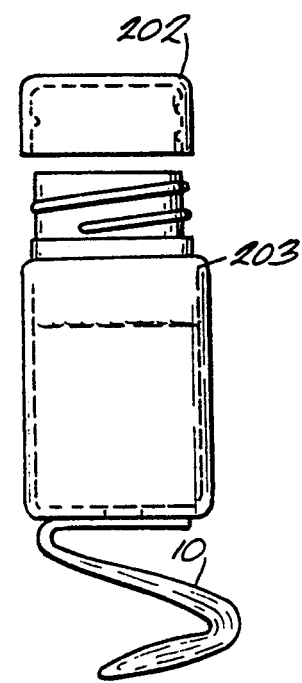
FIG. 12A illustrates a plastic bag coupled to the bottom of a bottle having a hole allowing the fluid specimen to be transferred to the plastic bag and FIG. 12B shows a plastic bag coupled to the side of a bottle having a hole allowing the fluid specimen to be transferred to and from the plastic bag.
Figure 12B:
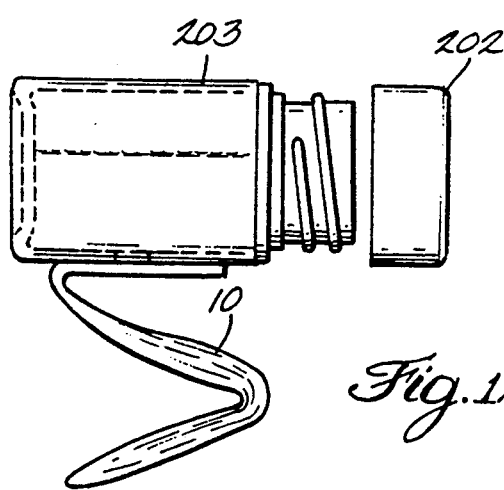

The structure of the mechanical sealing means not only acts to seal the plastic bag 10, 70 containing the specimen but also permits handling of the plastic bag independent of the support means. As shown in FIG. 7A the cylindrical sealing unit 118 is readily separated from the cylindrical support member 94. The sealed plastic bag 10, 70 and sealing unit 118 (seal member 98 and screw-on cap 102) can be easily transported by a technician to a compact storage unit (not shown). The sealing unit 118 also enables processing by an analytical technician who can conveniently gain access to selected portions of the plastic bag 10, 70 for specimen. The sealing unit 118 and the plastic bag 10, 70 can also be transferred to a shortened version of the cylindrical support member 94 for storage of the specimen in preparation for analysis. The disclosed mechanical sealing means has substantial versatility and can even be supported by the container 14 shown in FIG. 3 to collect the specimen. The illustrated mechanical sealing embodiments also do not require use of the thermal seal unit 36 in shown FIG. 4C, which can be inconvenient and difficult to use at certain specimen collecting sites.

In another embodiment the plastic bag 10, 70 can be held on the cylindrical support member 94 by retention means. The retention means enables easy and reliable transport to the technician of the collected specimen and with the technician then sealing the plastic bag 10, 70. Retention means can include, for example, retention posts 120 disposed on the exterior of either the sealing unit 118 or the cylindrical support member 94 (see in phantom on FIG. 7A). The plastic bag 10, 70 includes mating holes 124 which slip over the retention posts 120 thereby holding the plastic bag 10, 70 until sealed by the technician. Such an arrangement helps insure the specimen is not spilled before the plastic bag 10, 70 is sealed.

Figure 10A:
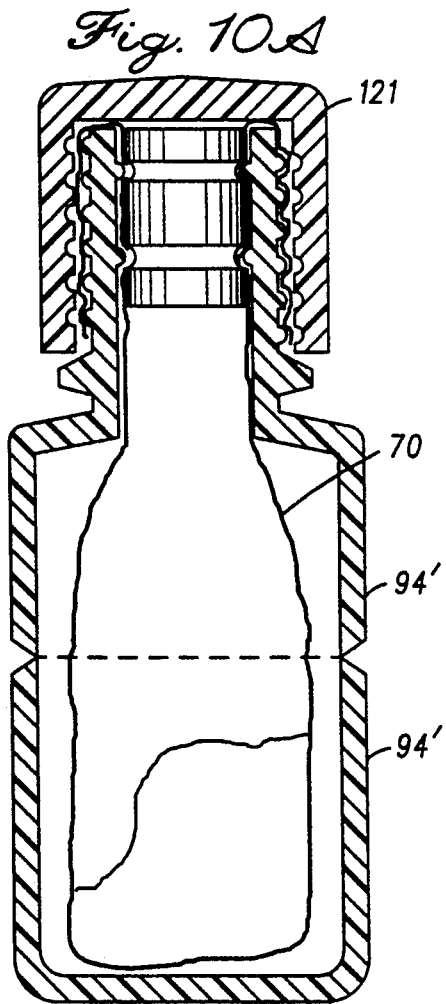
FIGS. 10A and 10B show a cross sectional view of a plastic bag support container having a breakaway feature for separating a top portion with the sealed bag attached.
Figure 10B:
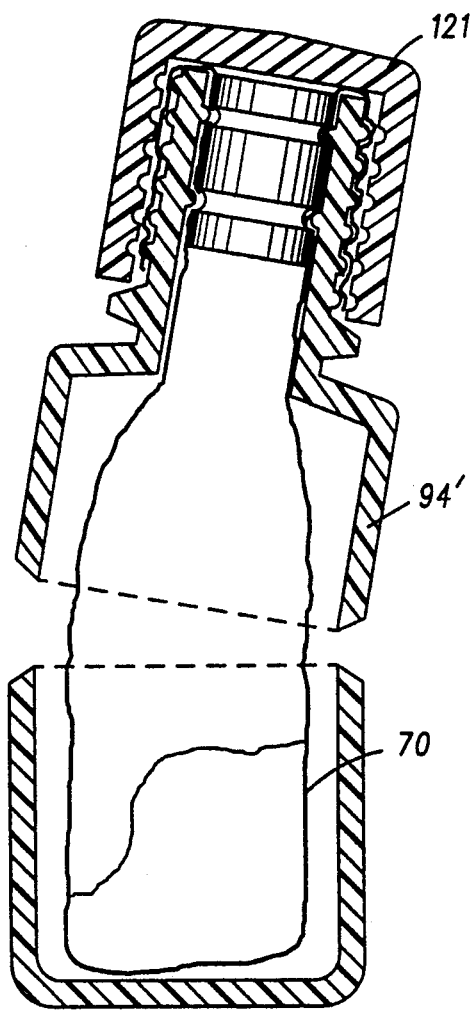

Another reliable form of retention means can include a separable form of the cylindrical support member 94' as shown in FIG. 10. On the left is shown the support member 94' having a scoring line or concave recession 95 which provides a line along which separation can be effected. The scoring line 95 allows removal of the upper portion of 94' supporting the plastic bag 70 as shown in the right view of FIG. 10. The separated sealed specimens can then be more conveniently stored and readily accessed by the technician who will perform testing of the specimen.

An additional form of retention means can include an elastic ring 126 which abuts and retains the fold over portion of the plastic bag 10, 70 in the manner shown in FIG. 7B. Another form of retention means can be a tapered form of either the cylindrical support member 94 or the sealing unit 118. One such form of retention means has a smaller diameter at the top compared to the distal end (see FIG. 7C). A slip ring 128 can then be placed into a snugly fitted position with the member 94, or as shown in FIG. 7C fitted onto the cylindrical seal member 98 thereby retaining the plastic bag 10, 70 in position.

Another feature of the embodiment of FIG. 7 is locking means for preventing movement of the sealing means relative to the support means. For example, in FIG. 7E is shown a keyway 134 in the sealing unit 118 and a mating key element 136 disposed on the cylindrical support member 94. Upon engaging the key element 136 with the keyway 134, relative rotation of the sealing unit 118 and the member 94 is prevented. This is particularly important when trying to seal the plastic bag 10, 70 using the threaded cylindrical seal member 98 and threaded seal portion 100 shown in FIG. 7A. A good seal would be difficult to achieve without such a locking means.

In a manner similar to the embodiments illustrated in FIG. 2A a tamper evident seal 130 can also be attached to the top of the seal cap 108 to ensure the specimen is not adulterated or modified prior to analysis (see exploded view of FIG. 7B).

Figure 8A:
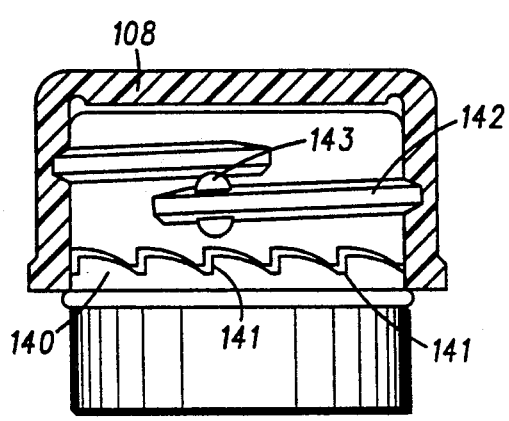
FIGS. 8A and 8B show two forms of thread structures of a sealing unit for preventing unsealing of a plastic bag once it has been sealed.
Figure 8B:
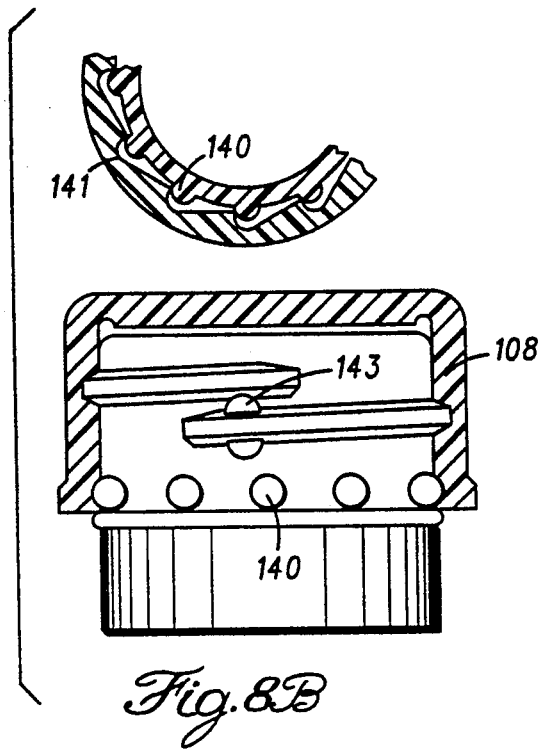
Figure 8C:
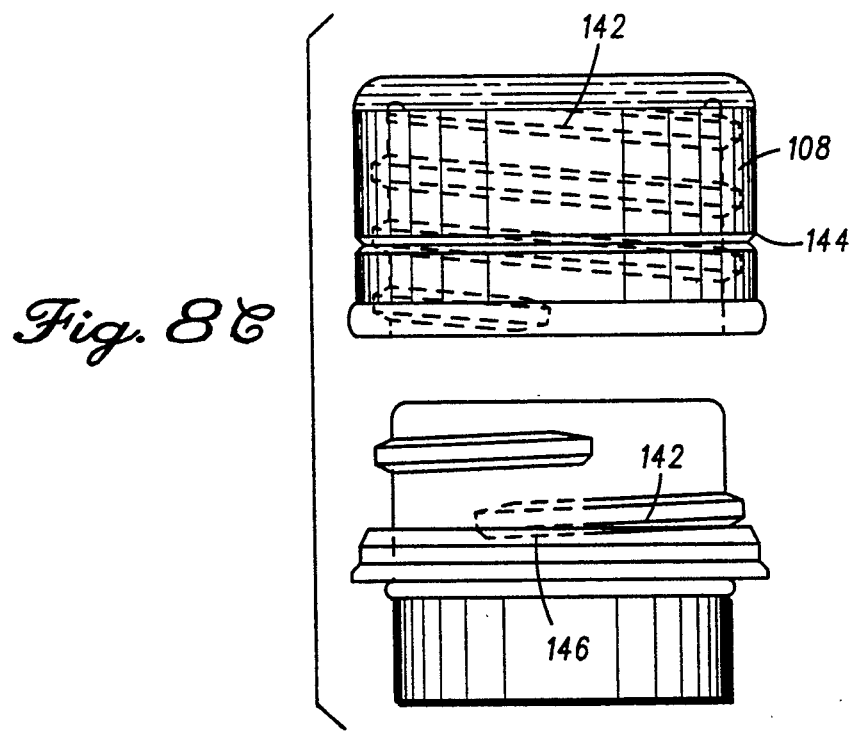
FIG. 8C illustrates a thread structure which prevents the resealing of the plastic bag once it has been unsealed.

Tampering with the specimen can also be discouraged by using a thread design for the mechanical sealing means which allows sealing of the plastic bag 10, 70 but either does not permit unsealing in any manner via the threaded portion or does not permit unsealing of the plastic bag 10, 70 without destruction of the sealing means. For example, as seen in FIG. 8A, several forms of circumferential obstacle structures 140 prevent turning of the cap 108 in any direction other than the sealing direction. As the cap 108 is turned to seal the plastic bag; recesses 141 along the cap periphery matingly engage the obstacle structure 140 which prevents any attempt to unseal the plastic bag. In another approach shown in FIG. 8B to preventing tampering with the specimen, the threads 142 have thread contours which allow sealing, however, upon unsealing easily recognizable damage is caused to the threads 142 by breaking away of a thin wall, cap ring 144. Thus, the accompanying damage to the adjacent inside threads 146 will prevent sealing after being unsealed. As a consequence, for purposes of analyzing the specimen, the technician must access the specimen in the plastic bag 10, 70 in another manner, making unauthorized unsealing and tampering more difficult.

Another feature of the mechanical sealing means is concerned with design control of the ratchet type obstacle structure 140 shown in FIG. 8A. The structure 140 allows turning in the sealing direction only. In a further refinement of the structure 140, once the seal is effectuated, a mechanical stop 143 (or other equivalent means) prevents exceeding a maximum mechanical stress level of the structure 140 and providing breakage thereof. In this manner, the cap 108 can be tightened sufficiently to ensure a good seal, but cannot be overtightened, which would lead to failure of the cap 108 and loss of the accompanying seal.

Figure 11A:
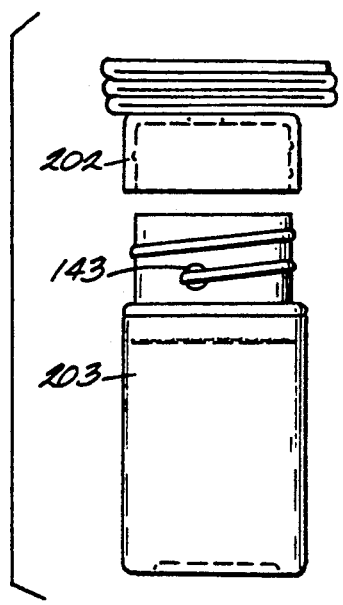
FIG. 11A illustrates a folded plastic bag coupled to a bottle cap disposed above a bottle containing a fluid specimen.
Figure 11B:
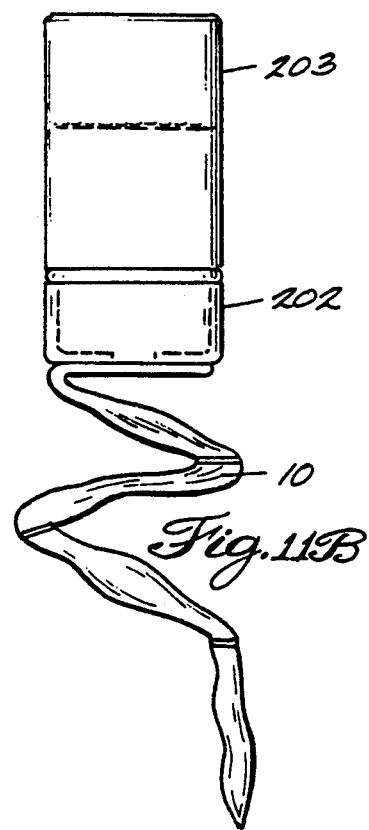
FIG. 11B shows the transfer of the fluid specimen from the bottle to the plastic bag or vice versa.
Figure 11C:
FIG. 11C shows a catheter coupled into a plastic bag.
Figure 11D:
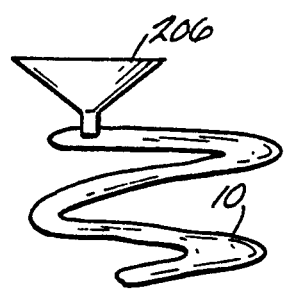
FIG. 11D illustrates a funnel coupled into a plastic bag and FIG. 11E shows a piece of tubing coupled into a plastic bag.
Figure 11E:
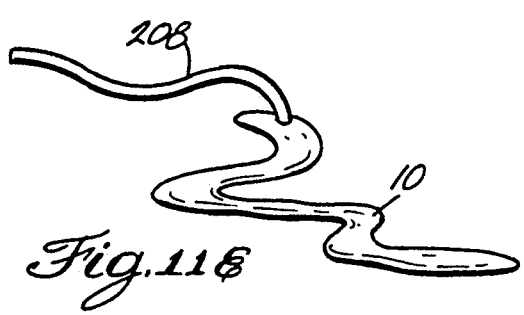

In another form of the invention, the multicompartment plastic bag 10 can be coupled to general means for transferring the specimen to the bag 10. The transfer means can, for example, include a bottle cap 202 (FIG. 11b) a catheter 204, (FIG. 11c), a funnel 206 (FIG. 11d) or tubing 208 (FIG. 11e). These various transfer means can be connected at any desired location on the plastic bag 10, such as the top, bottom or side of the plastic bag 10. These transfer means allow the convenient transfer of the specimen from the source (e.g., a remote or local container or transfer lines) to the plastic bag 10. The transfer means can also be used to couple directly into the source for a less conventional, but sometimes necessary, collection of the specimen.

Some of these transfer features allow the collection of the specimen independent of the subject and even processing of the specimen before transfer into the bag 10. For example, (a) the bottle cap 202 and attached plastic bag 10 can be joined to a bottle 203 which contains the specimen to be transferred, (b) the funnel easily allows pouring the specimen into the plastic bag 10, (c) the catheter 204 enables the transfer of the specimen directly and (d) the tubing allows the general transfer of the specimen from any source, such as a reservoir (not shown). These transfers therefore allow the hybrid use of the multicompartment plastic bag 10 with more conventional devices (e.g., bottles) for accumulation of specimens.

In another form of the invention as shown in FIG. 13 the twist cap 150 includes a threaded section 151 enabling opening of the twist cap 150 to remove the desired amount of fluid specimen. Before the user can obtain the fluid specimen the user must remove or otherwise destroy obstruction 152, thereby providing evidence of tampering, or previous access to, the plastic bag 10. Also shown is the larger port 159 with a ratchet type of cap 153 which allows engagement but not disengagement. Alternatively, the cap 153 can be of the variety which includes installation of seal 162 after filling the plastic bag 10 through the port 159.

The plastic bag 10 can also include an access port 168 with a test tube 170 coupled thereto by a thin break away section 172. The fluid specimen can thus be collected in the test tube 170, passing through the port 168 connected to one of the bag subcompartments, and the fluid specimen is then removed for testing. One can also couple a test tube (not shown) to the access port 168 using a shrink wrap or other tamper evident means which completes a seal to the access port 168. Upon removal of the tamper evident means there is provided clear evidence of use or tampering with the associated specimen.

While preferred embodiments of the invention have been shown and described, it will be clear to those skilled in the art that various changes and modifications can be made without departing from the invention in its broader aspects as set forth in the claims provided hereinafter.

What is claimed is:

1. An automated method of sampling a fluid specimen using a plastic container and testing the fluid specimen at an analysis station, said plastic container having at least one access port with an access port housing sealingly coupled to said container, said method comprising the steps of:

positioning said plastic container adjacent to a specimen sampling station having a test receptacle;

moving a piercing element positioned on an opening top of said test receptacle with said sampling station and said test receptacle to puncture said access port housing while said piercing element is engaging said port housing;

draining the fluid specimen through said access port housing and said piercing element into said test receptacle;

resealing said access port housing using said piercing element; and transporting the fluid specimen in said test receptacle to said analysis station.

2. The method as defined in claim 1 further including the step of applying pressure to said plastic container to controllably force said fluid specimen into said test receptacles.

3. The method as defined in claim 1 wherein said test receptacle is selected from a test tube, a glass tube, or a breakaway tube, said piercing element being integrally coupled to said receptacle.

4. The method as defined in claim 1 wherein said step of positioning said plastic container comprises moving said plastic container on a conveyor belt.

5. The method as defined in claim 4 wherein said plastic container access port housings being matingly received in openings of said conveyor belt.

6. The method as defined in claim 1 further including bar code identification on said plastic container access port housing for enabling identification of said fluid specimens in each of said plastic container.

7. The method as defined in claim 1 wherein said access port housing is substantially concave in shape.

8. An automated method of sampling and testing including a specimen sampling station for collecting a fluid specimen in a plastic container having at least one access port with an access port housing sealingly coupled to said container and an analysis station for analyzing said fluid specimen, said method comprising the steps of:

positioning said plastic container adjacent said specimen sampling station having a test receptacle;

moving a piercing element positioned on an opening top of said test receptacle with said sampling station and said test receptacle to puncture said access port housing while said piercing element is engaging with said access port housing;

draining the fluid specimen through said access port housing and said piercing element into said test receptacle;

transferring said piercing element from said sampling station to said plastic container;

resealing said access port housing using said piercing element; and transporting the fluid specimen in said test receptacle to said analysis station.

9. An automated method of sampling and testing including a specimen sampling station for collecting a fluid specimen in a plastic container having at least one access port with an access port housing sealingly coupled to aid container, and an analysis station for analyzing said fluid specimen said method comprising the steps of:

positioning said plastic container adjacent said specimen sampling station having a test receptacle;

moving a piercing element positioned on an opening top of said test receptacle with said sampling station and said test receptacle to puncture said access port housing while said piercing element is engaging said port housing;

draining the fluid specimen through said access port housing and said piercing element into said test receptacle;

displacing said plastic container to assist in draining the fluid specimen from said plastic container;

resealing said access port housing using said piercing element; and transporting the fluid specimen in said test receptacle to said analysis station.

* * * * *